United States Patent
Kawabata et al.

(10) Patent No.: US 7,125,387 B2
(45) Date of Patent: Oct. 24, 2006

(54) ULTRASONIC APPARATUS FOR THERAPEUTICAL USE

(75) Inventors: Kenichi Kawabata, Kodaira (JP); Nami Sugita, Ranzan (JP); Shinichiro Umemura, Hachioji (JP); Takashi Azuma, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 434 days.

(21) Appl. No.: 10/368,436

(22) Filed: Feb. 20, 2003

(65) Prior Publication Data

US 2004/0044298 A1 Mar. 4, 2004

(30) Foreign Application Priority Data

Aug. 28, 2002 (JP) ............... 2002-248206

(51) Int. Cl.
*A61H 1/00* (2006.01)
*A61B 8/00* (2006.01)

(52) U.S. Cl. ............... 601/2; 600/407; 600/437; 600/439

(58) Field of Classification Search ............... 601/2–4; 600/407–439
See application file for complete search history.

(56) References Cited

U.S. PATENT DOCUMENTS

| 5,158,071 A | 10/1992 | Umemura et al. |
| 5,523,058 A | 6/1996 | Umemura et al. |
| 5,556,372 A | 9/1996 | Talish et al. |
| 5,626,554 A * | 5/1997 | Ryaby et al. ............... 601/2 |
| 5,730,705 A * | 3/1998 | Talish et al. ............... 601/2 |
| 5,762,616 A * | 6/1998 | Talish ............... 601/2 |
| 2003/0135135 A1 * | 7/2003 | Miwa et al. ............... 601/2 |

FOREIGN PATENT DOCUMENTS

| EP | 0538241 | 4/1993 |
| JP | 01-146829 | 6/1989 |
| JP | 2002-165858 | 6/2002 |
| WO | 94/06380 | 3/1994 |
| WO | 98/01131 | 1/1998 |
| WO | 98/52610 | 11/1998 |
| WO | 00/71207 | 11/2000 |
| WO | 00/76406 | 12/2000 |

* cited by examiner

*Primary Examiner*—Brian L. Casler
*Assistant Examiner*—Baisakhi Roy
(74) *Attorney, Agent, or Firm*—Antonelli, Terry, Stout and Kraus, LLP.

(57) ABSTRACT

According to the invention, an ultrasonic apparatus for therapeutical use suitable for remedy by the irradiation of an ultrasonic wave low in the degree of convergence using medicine that stays in a disease region, reduces the threshold of cavitation caused by an ultrasonic wave and secondarily generates active oxygen by the acoustic cavitation caused by the ultrasonic wave is provided. The ultrasonic apparatus for therapeutical use is provided with a belt wearable in a position (on the abdomen of a patient) that surrounds a diseased part and unit ultrasonic radiators can be mounted in an arbitrary position of the belt.

15 Claims, 8 Drawing Sheets

ULTRASONIC APPARATUS FOR THERAPEUTICAL USE

FIELD OF THE INVENTION

The present invention relates to an apparatus for ultrasonic irradiation for therapeutical use operated by a patient himself/herself even without the presence of a doctor such as home remedy.

BACKGROUND OF THE INVENTION

The remedy of a malignant tumor by the radiation of focused ultrasound from the outside of a living body is less invasive, compared with surgery and is excellent in principle in relation to the deterioration of the physical strength during an operation of a patient, the recovery after the operation and the enhancement of the quality of life. Therefore, in future, the social value is considered to be enhanced.

One of remedies using focused ultrasound uses thermal effect that ultrasonic energy by a radiated ultrasonic wave is absorbed by a living tissue and hereby, the temperature of a disease region rises. The other one uses chemical interaction between a chemical substance existing in a disease region and a radiated ultrasonic wave. Of the latter, a remedy using a substance that generates active oxygen when an ultrasonic wave is radiated is proposed by Umemura and others and is named a sonodynamic therapy. Acoustic cavitation is considered to play an important role in a mechanism in which therapeutical effect is obtained by the sonodynamic therapy.

For a method of efficiently causing and collapsing acoustic cavitation for this purpose, heretofore, only physical means have been proposed. In a U.S. Pat. No. 2,741,907, technique for switching a sound field at an interval of 0.01 to 10 milliseconds (ms) and radiating an ultrasonic wave is reported. According to this technique, an ultrasonic wave is radiated, switching sound fields different in a wave front at an interval of the above time in consideration of a fact that ultrasonic irradiation time required for causing acoustic cavitation is 0.01 to 10 ms and a cycle that acoustic cavitation caused by one sound field is collapsed by the other sound field is repeated. Hereby, the efficiency of sonochemical reaction can be improved by an order of magnitude with the same ultrasonic power, compared with a case that sound fields are not switched.

Also, in the U.S. Pat. No. 5,523,058, technique in which an ultrasonic wave having a waveform advantageous for causing acoustic cavitation, which normally obtained only in the presence a reflector, without an reflector is disclosed. In the technique, a waveform advantageous for causing acoustic cavitation is acquired by superimposing its double frequency on one frequency component. As the effect of a reflector cannot be necessarily expected when an ultrasonic wave is radiated on a living body, the technique is expected to contribute to the increase of the effect and the enhancement of safety in remedy by ultrasonic irradiation.

Also, in Japanese published examined patent application No. Hei6-29196, for a method of chemically enhancing the anti-tumor effect of an ultrasonic wave, a method of using a substance that generates active oxygens by the chemical effect of ultrasound exposure is reported. A substance such as porphyrin used in the technique has a function of secondarily generating active oxygen by acoustic cavitation caused by an ultrasonic wave, however, the substance could not reduce the threshold of cavitation. In the meantime, in WO98/01131, a method of reducing the threshold of cavitation by an amphiphilic xanthene dye sensitizer and secondarily generating active oxygen by acoustic cavitation caused by an ultrasonic wave is proposed.

The social evaluation of minimally invasive remedy in which therapeutical effect is acquired by causing acoustic cavitation using focused ultrasound is considered to increase in future. In case an ultrasonic wave is used, there is no problem that a patient is exposed, compared with other less invasive remedy such as a heavy ion particle radiotherapy and radiation therapy and the miniaturization of an apparatus is easy. Therefore, the use by a patient himself/herself except a hospital under the suitable direction of a doctor such as home remedy may be capable.

However, home remedy using a conventional type apparatus using a convergent ultrasonic wave has a problem related to focusing. That is, as known from the above well-known examples, a conventional type apparatus using focused ultrasound premises that after a diseased part and its state are specified by diagnosis based upon images and biopsy, a convergent ultrasonic wave is focused on the disease region and is precisely radiated. This reason is that when the convergent ultrasonic wave is focused off the disease region, a non-disease region of a human body is damaged. To radiate a precisely focused ultrasonic wave, a medical apparatus for imaging disease regions is required. However, currently, no medical apparatus is available which is small enough for home use and at the same time capable of targeting disease regions. Further, to decide the location and the state of a disease region based upon images by the current medical image diagnostic apparatus, expert knowledge is required and non-expert patients cannot target a disease region.

SUMMARY OF THE INVENTION

Therefore, in the invention, an ultrasonic wave that irradiates a large range including a diseased part is used in place of a conventional focused ultrasonic wave. Even if a part out of disease region is irradiated by an ultrasonic wave, a non-disease region of a human body is hardly damaged because the, degree of convergence of the radiated ultrasonic wave is low. In the meantime, this means that the effect of the irradiation of an ultrasonic wave on a disease region is small, however, this proposes that effect close to remedy by the irradiation of focused ultrasound is acquired as a result by supplementing the small effect of the irradiation of the ultrasonic wave by the effect of medicine that remains in the disease region. That is, it can be said that the invention remarks that medicine that stays in a diseased part for long time and enhances the effect of an ultrasonic wave exists and proposes therapy without using an ultrasonic wave high in the degree of convergence.

DESCRIPTION OF THE PREFERRED EMBODIMENTS

Figure 1:
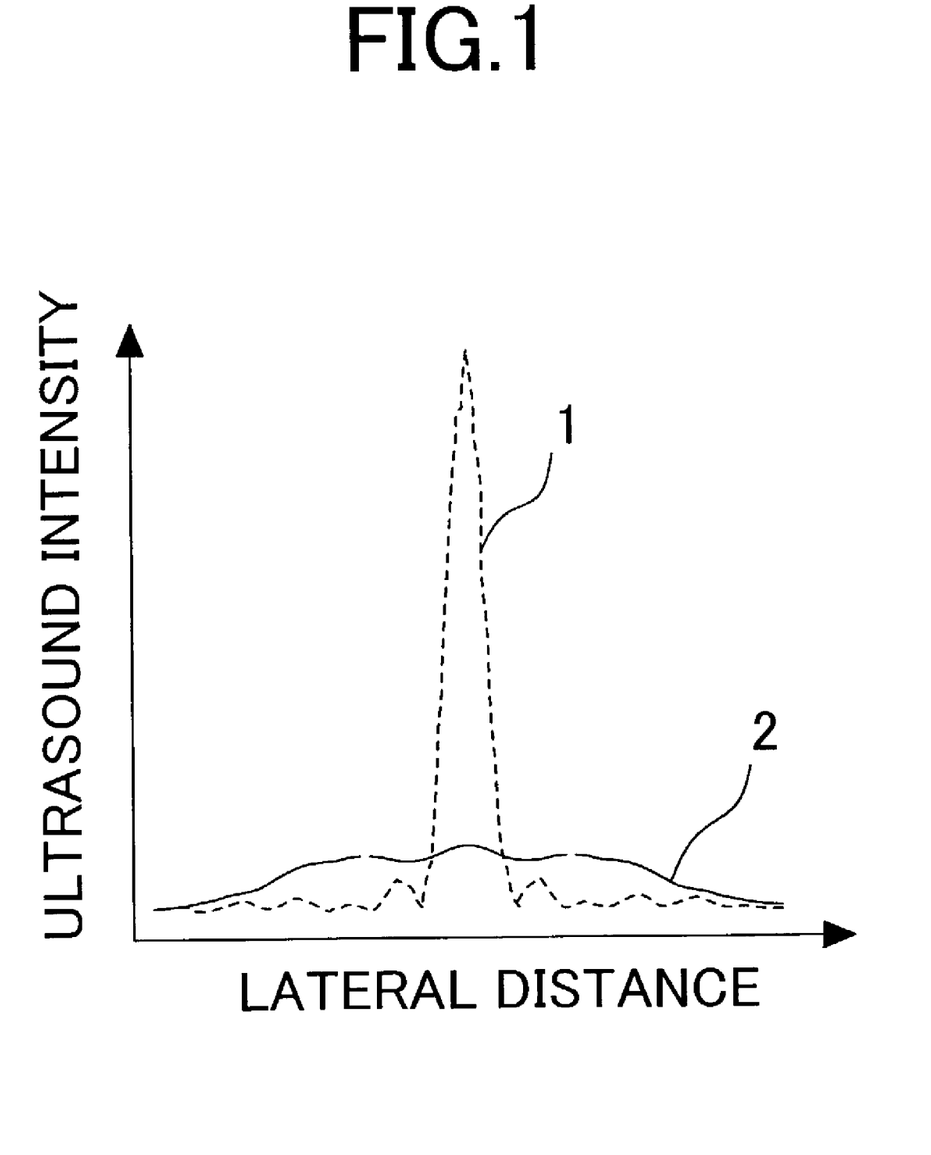
FIG. 1 shows a typical focused acoustic field and a typical unfocused acoustic field.

FIG. 1 shows a typical focused acoustic field and a typical unfocused acoustic field. A reference number 1 denotes the intensity of a sound field by the radiation of a focused acoustic and 2 denotes the intensity of a sound field by the radiation of an unfocused ultrasound with low degree of convergence. In FIG. 1, each ultrasound source shall have the same power. That is, it shows that in case an ultrasonic wave having the same energy from a sound source having the same area as the other is converged and radiated, it irradiates a smaller range at stronger intensity and in case the other ultrasonic wave is radiated without being converged, it irradiates a larger range than the area of its sound source. The intensity at a focal position of a radiated convergent wave is also shown.

If a large range can be irradiated as described above, the low precision of focusing is not hindrance. As an ultrasonic wave having the similar intensity to intensity in a disease region is also radiated near side and far side of the disease region independent of the position of the diseased part as shown as the intensity of the sound field 2 in case the degree of convergence is low, a mechanism for discriminating the diseased part and the other part without depending upon the convergence of an ultrasonic wave and acquiring therapeutical effect only in the diseased part is required.

For such a mechanism, the invention remarks an amphiphilic xanthene dye sensitizer proposed in WO98/01131 and proposes the effectiveness of remedy by the synergistic effect of this medicine and ultrasonic irradiation. As shown in WO98/01131, an alkylated derivative of Rose Bengal which is xanthene dye has the following three properties.

(1) Accumulating in tumor tissue
(2) Promoting the generation of acoustic cavitation by ultrasonic irradiation
(3) Producing anti-tumor effect when the acoustic cavitation occurs In case the alkylated derivative of Rose Bengal is administrated even if an ultrasonic wave having the same intensity is respectively radiated on tumor tissue and normal tissue, acoustic cavitation more easily occurs than in the normal tissue by the derivative existing at higher concentration in the tumor tissue, and the anti-tumor effect can be acquired, reducing damage to the normal tissue. That is, even if the degree of ultrasonic convergence is low and the intensity of a radiated ultrasonic wave is low, the anti-tumor effect can be acquired by the effect by the medicine.

First Embodiment

Figure 2:
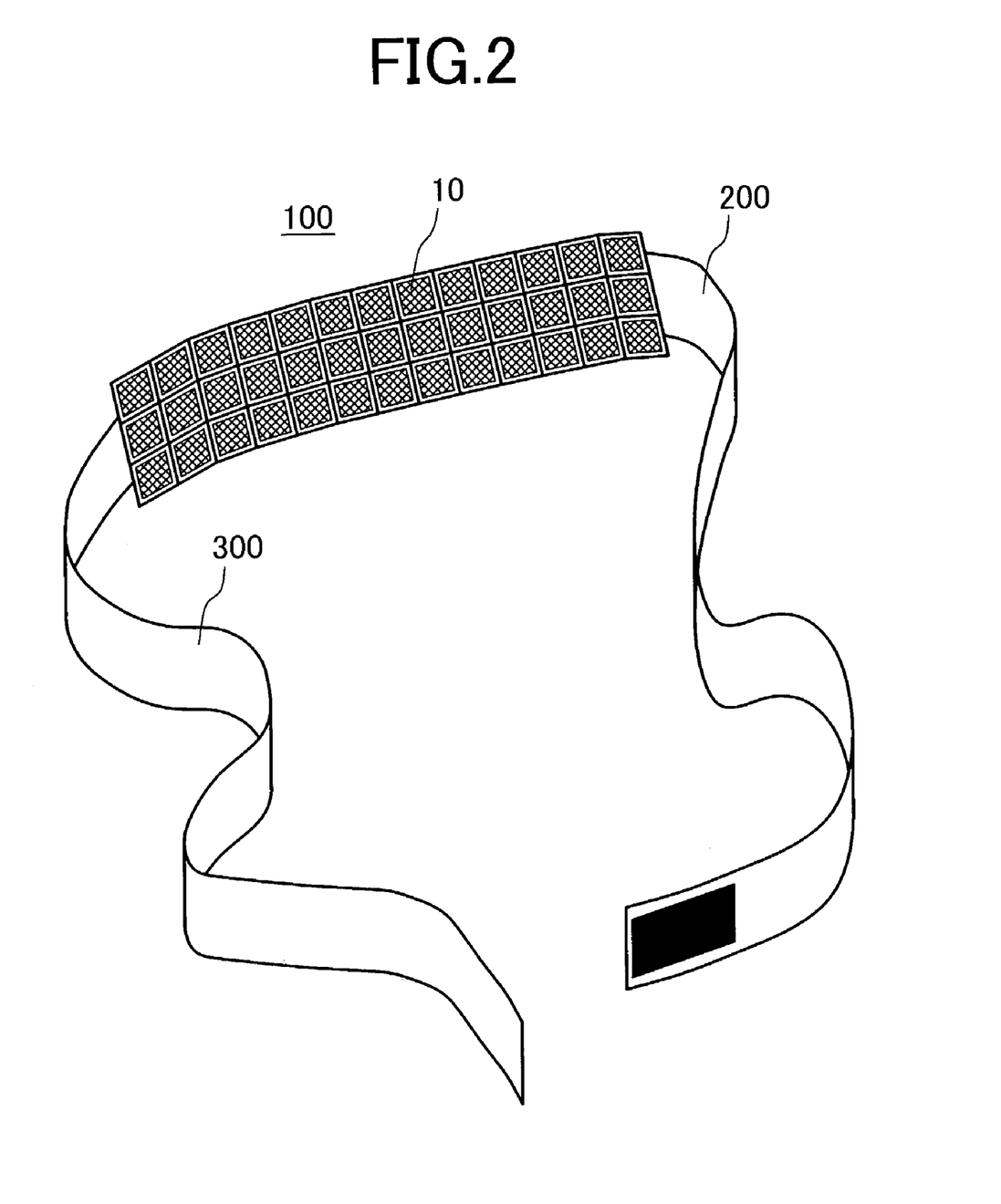
FIG. 2 is a conceptual drawing showing an ultrasonic wave radiating apparatus which covers the abdomen of a patient and in which multiple unit ultrasonic radiators are flatly arranged and mounted as a first embodiment of the invention.

FIG. 2 is a conceptual drawing showing an ultrasonic wave radiating apparatus which covers the abdomen of a patient and on which multiple ultrasonic transducer elements are arranged flatly and mounted as a first embodiment of the invention. As shown in FIG. 2, a reference number 10 denotes a ultrasonic transducer element and in FIG. 2, the ultrasonic wave radiating apparatus 100 is composed of (3×13) pieces of ultrasonic transducer elements 10. Reference numbers 200 and 300 denote bands for fixing the ultrasonic wave radiating apparatus 100 on the abdomen of the patient and they are fixed to both sides of the ultrasonic wave radiating apparatus 100. A doctor directs the patient about the installation and the usage of the ultrasonic wave radiating apparatus 100 and the injection of medicine in the patient himself/herself.

Figure 3:
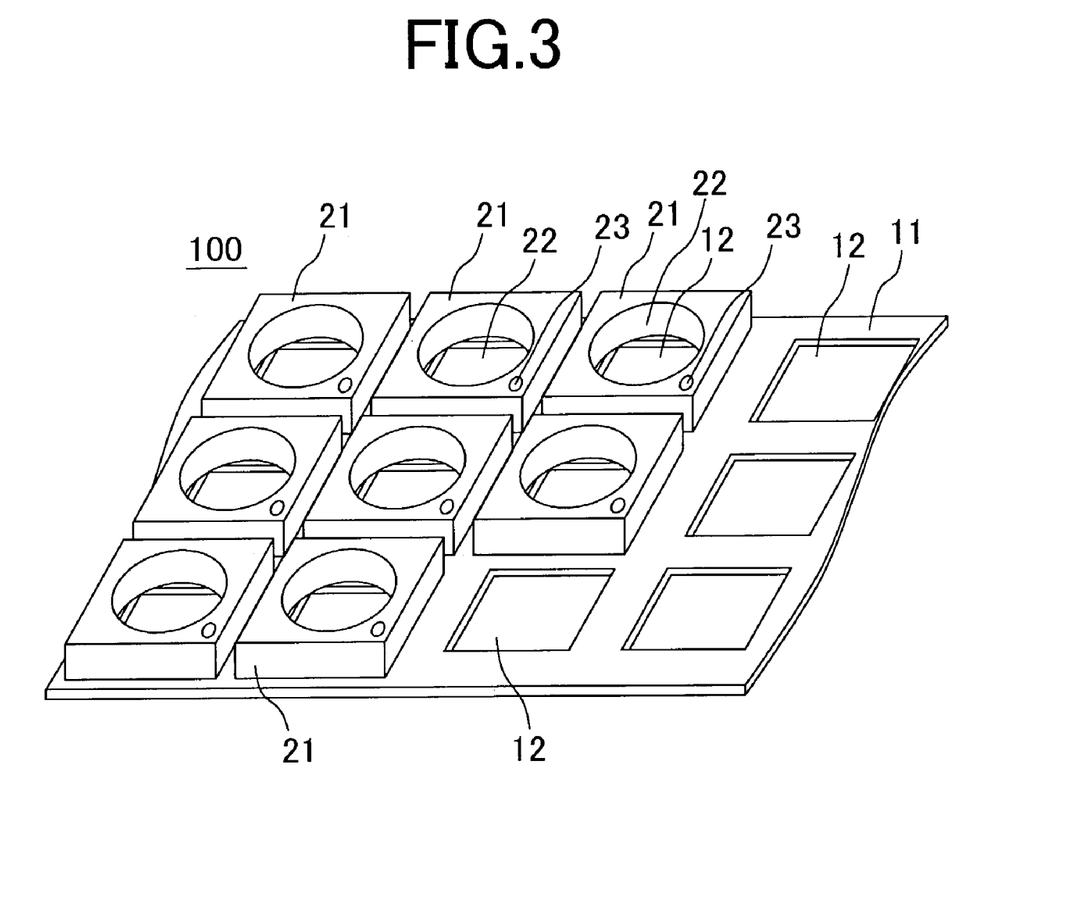
FIG. 3 is an enlarged view showing a part of an ultrasonic wave radiating apparatus 100 from which a part of components is removed.

FIG. 3 is an enlarged view in which a part of components is removed showing an enlarged part of the ultrasonic wave radiating apparatus 100. A reference number 11 denotes a substrate of the ultrasonic wave radiating apparatus 100 and the substrate is made of elastic material so that the ultrasonic wave radiating apparatus 100 can adhere to the surface of the abdomen of the patient as much as possible when the apparatus is wound on the abdomen of the patient. For example, the substrate is made of a silicone sheet 1 to 2 mm thick. A reference number 12 denotes an opening provided periodically inside the substrate. The opening is arranged corresponding to the ultrasonic transducer element 10 and for example, has the size of 30×30 mm. A reference number 21 denotes a holder and the holder has a circular opening 22 substantially including the opening 12. For example, the holder 21 is approximately 15 mm thick and the inside of each opening 22 is threaded. Each holder 21 is arranged so that the respective central positions of the opening 12 and the opening 22 are coincident and is stuck on one surface of the substrate 11. Further, an opening 23 is provided to one of the corners of the holder 21. The ultrasonic transducer element 10 is mounted on the holder 21 as described later.

Figure 4A:
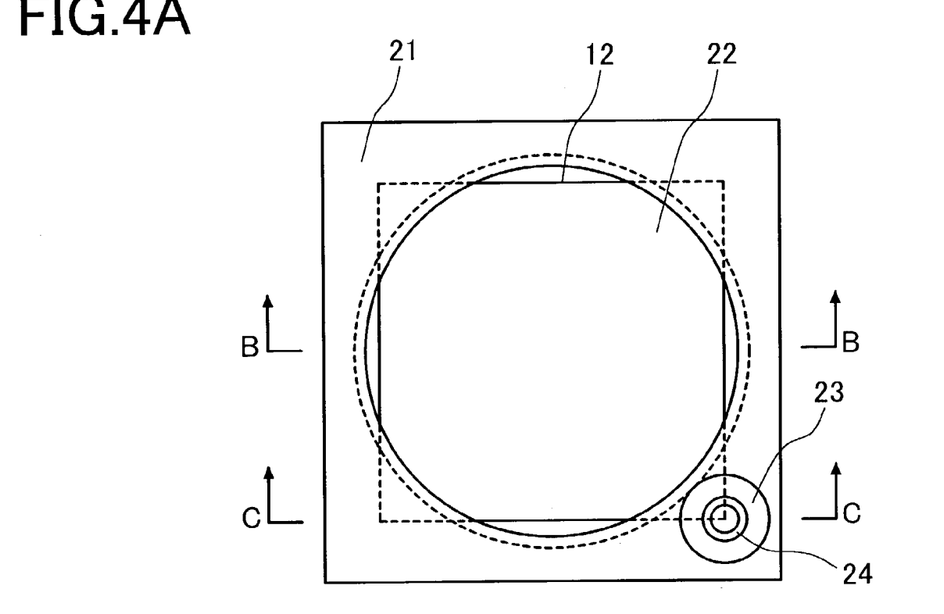
FIG. 4A is a top view showing a holder 21.
Figure 4B:
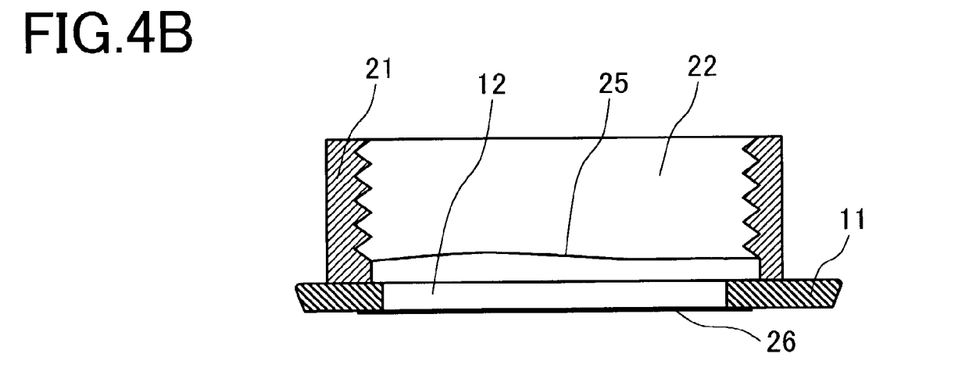
FIG. 4B is a sectional view viewed-along an arrow B—B in FIG. 4A
Figure 4C:
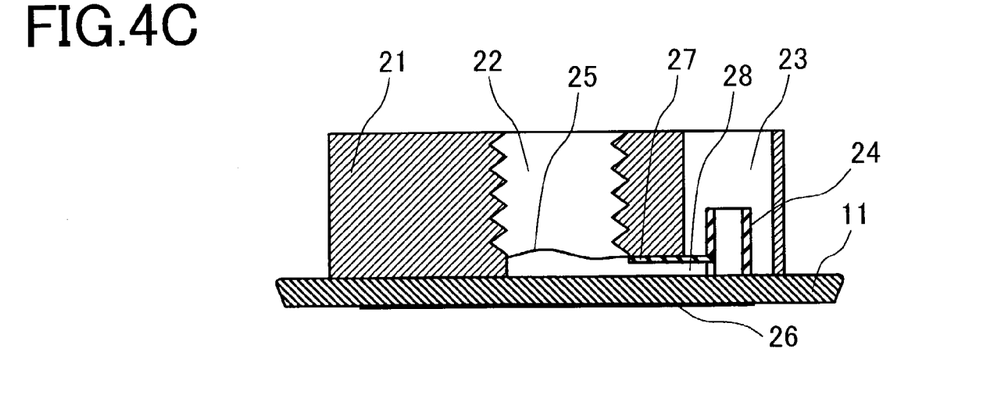
FIG. 4C is a sectional view viewed along an arrow C—C in FIG. 4A.

FIG. 4A is a top view showing the holder 21, FIG. 4B is a sectional view viewed along an arrow B—B and FIG. 4C is a sectional view viewed along an arrow C—C. The holder 21 is stuck to one surface of the substrate 11 so that the opening 22 of the holder 21 substantially covers the opening 12 of the substrate 11 as described above and is overlapped with the opening 12. The opening 23 is provided at one corner of the holder 21 and a hollow protrusion 24 is provided to the substrate 11 in the central position of the opening 23. An extremely thin and elastic shielding film 25 is provided to the end near to the substrate 11 of the holder 21. A thin shielding film 26 is provided to the surface on the reverse side of the surface on which the holder 21 is stuck of the opening 12 of the substrate 11. For example, the film is a cellulose filter of 50 μm and is approximately 0.5 mm or less thick. An opening is provided to a part contact to the substrate 11 of the hollow protrusion 24 provided to the central position of the opening 23 and a communicating part 28 is formed between the inside of the protrusion 24 and space under the shielding film 25 of the holder 21. A reference number 27 denotes a partition for the communicating part.

Figure 5A:
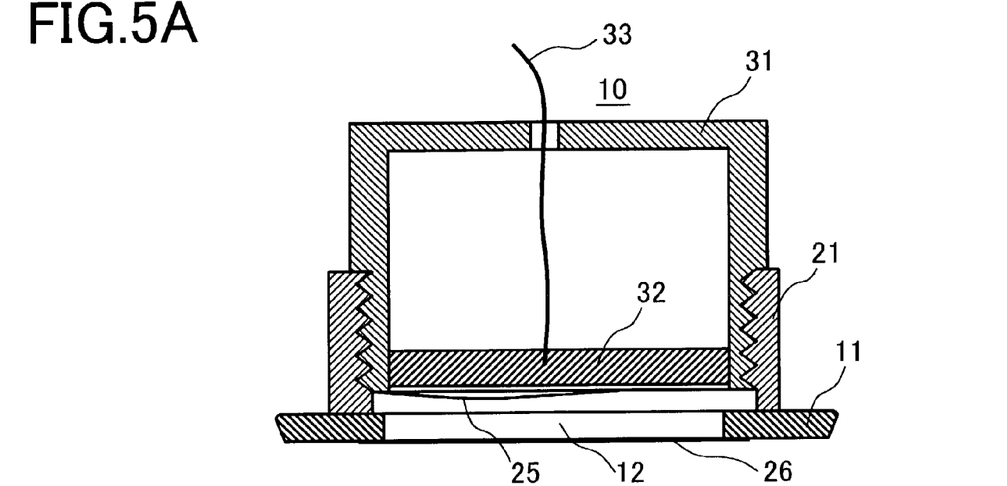
FIG. 5A is a sectional view showing a state in which an ultrasonic transducer element 10 is installed in an opening 22 of the holder 21 and viewed along the arrow B—B in FIG. 4A.
Figure 5B:
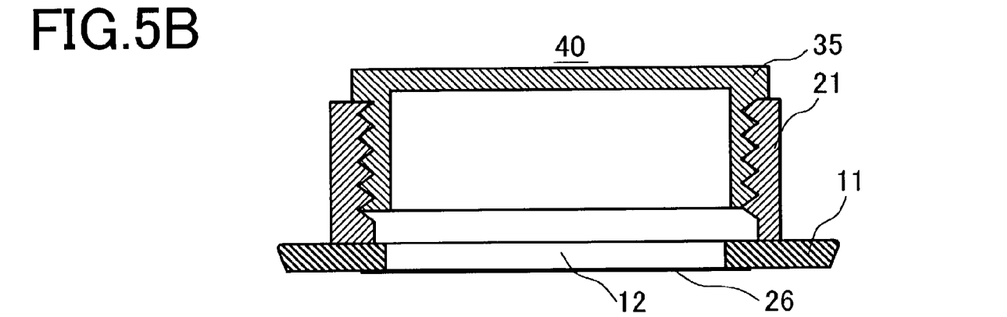
FIG. 5B is a sectional view showing a state in which a dummy 40 is installed in place of the ultrasonic transducer element 10 and viewed along the arrow B—B in FIG. 4A
Figure 5C:
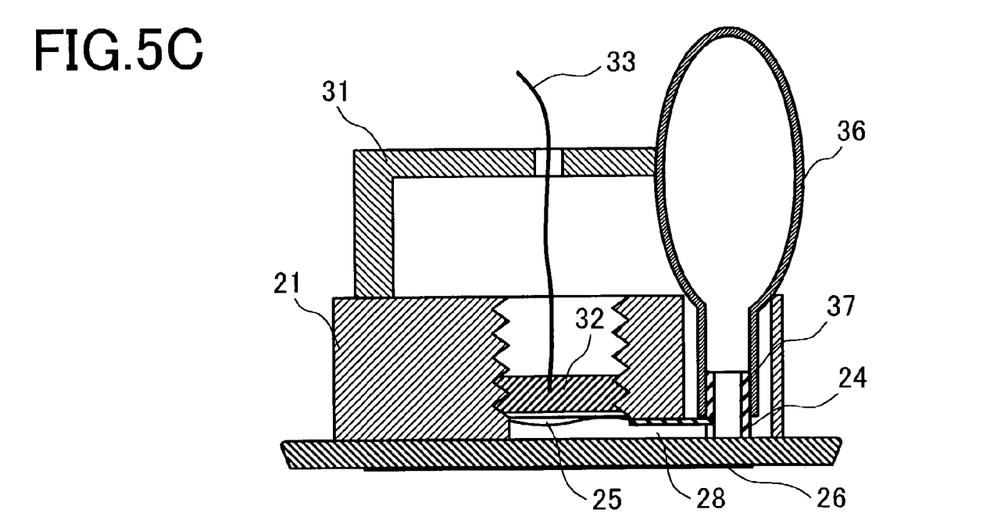
FIG. 5C is a sectional view showing a state in which the ultrasonic transducer element 10 is installed in the opening 22 of the holder 21 and a holder 36 including ultrasonic jelly (acoustic coupling media) inside is mounted on a protrusion 24 in an opening 23 and viewed along the arrow C—C in FIG. 4A.

FIG. 5A is a sectional view showing a state in which the ultrasonic transducer element 10 is installed in the opening 22 of the holder 21 and viewed along the arrow B—B in FIG. 4A, FIG. 5B is a sectional view showing a state in which a dummy 40 is installed in place of the ultrasonic transducer element 10 and viewed along the arrow B—B in FIG. 4A and FIG. 5C is a sectional view showing a state in which the ultrasonic transducer element 10 is installed in the opening 22 of the holder 21 and a holder 36 including ultrasonic jelly (acoustic coupling media) inside is mounted on the protrusion 24 in the opening 23 and viewed along the arrow C—C shown in FIG. 4A.

The ultrasonic transducer element 10 is composed of a cylindrical cover 31, a piezoelectric transducer 32 provided in the cylindrical cover and a cable 33 for supplying alternating voltage having a predetermined frequency to the piezoelectric transducer. The piezoelectric transducer 32 is formed by a plane piezoelectric element. A screw is formed on the circumference at the end of the cover 31 so that the screw is engaged with a screw provided to the circumference of the opening 22 of the holder 21. The cover 31 is turned so that the screws are engaged and is inserted into the opening 22 of the holder 21. In a state in which the unit ultrasonic radiator 10 is fully press-fitted into the opening 22 of the holder 21 and the installation is completed, as shown in FIG. 5A, the piezoelectric transducer 32 is in contact with the shielding film 25.

In the meantime, the dummy 40 is installed in the opening 22 of the holder 21 in which no ultrasonic transducer element is installed. The dummy 40 is formed by only a cylindrical cover 35. The dummy 40 is provided only to prevent dust and others from entering the inside of the opening 22 of the holder 21 in which no ultrasonic transducer element 10 is installed. In FIG. 5B, the opening 23 is not shown, however, to prevent dust and others from entering the inside of the opening 23 of the holder 21, it is desirable that a cap is also provided to the opening 23.

The holder 36 is mounted by inserting the protrusion 24 in the opening 23 of the holder 21 in which the ultrasonic transducer element 10 is installed into a guide 37 of the holder 36 including the ultrasonic jelly (the acoustic coupling media) inside. As a result, as shown in FIG. 5C, space between the shielding film 25 and the shielding film 26 communicates with the inside of the holder 36 via the communicating part 28. When the ultrasonic jelly (the acoustic coupling media) in the holder 36 is pushed out into the space between the shielding film 25 and the shielding film 26 by pressing the holder 36 manually in this state, the ultrasonic transducer element 10 can be touched to the skin of the abdomen of the patient which is in contact with the piezoelectric transducer 32 via the shielding film 26 without via air.

Figure 6:
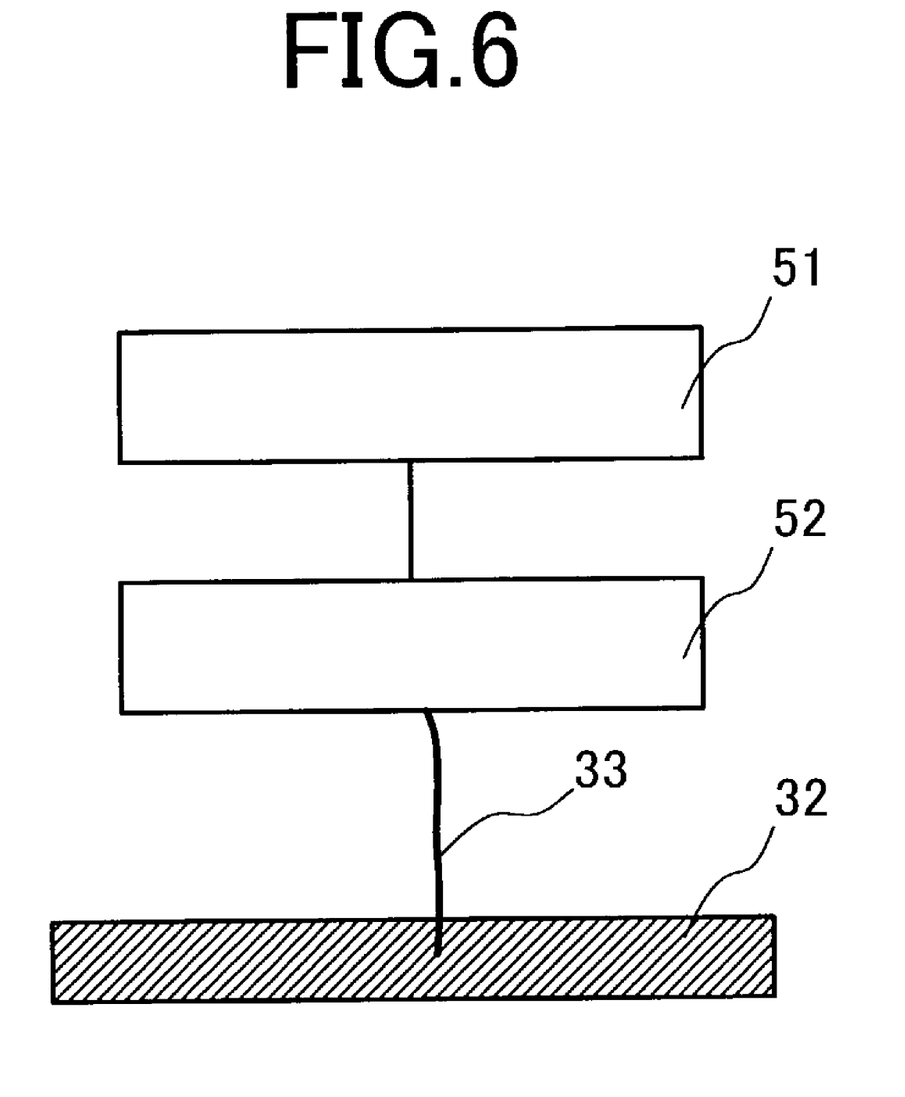
FIG. 6 shows a control system of the ultrasonic wave radiating apparatus 100.

FIG. 6 shows a control system of the ultrasonic wave radiating apparatus 100. A reference number 51 denotes a controller mainly formed by a personal computer in which a required program is built, 52 denotes an ultrasonic signal generating/amplifying circuit and the ultrasonic signal generating/amplifying circuit generates an ultrasonic signal having a cycle and magnitude according to a signal from the controller 51. The output of the ultrasonic signal generating/amplifying circuit 52 is applied to the piezoelectric transducer 32 via the cable 33. The program of the controller 51 is set so that a control signal according to a state of the patient is output. The controller 51 and the ultrasonic signal generating/amplifying circuit 52 respectively shown in FIG. 6 may be also individually installed in the cover 31 of the unit ultrasonic radiator 10 and only the ultrasonic signal generating/amplifying circuit 52 may be also individually installed. Needless to say, as shown in FIG. 5A, only the piezoelectric transducer 32 may be also installed in the cover 31. The units which are not installed in the cover 31 may be also installed in one of the dummies and a signal required for each ultrasonic transducer element 10 may be also supplied from the dummy.

As described above, in the first embodiment, the unit ultrasonic radiator 10 and the holder 36 including the ultrasonic jelly (the acoustic coupling media) inside are installed in the holder 21 corresponding to a location to be remedied of the patient and the dummy 40 is installed in the other holder 21. Therefore, the doctor first directs the patient about how to wear the ultrasonic wave radiating apparatus 100 and determines in which position the ultrasonic transducer element 10 is to be mounted in the stablest state of installation. Next, the doctor directs the patient about how to inject medicine mainly made of an alkylated derivative of Rose Bengal which is xanthene dye into the patient himself/herself and directs the patient about how to activate each ultrasonic transducer element 10 of the ultrasonic wave radiating apparatus 100 after injection. The activation means both the activation of the controller 51 and operation for pressing the holder 36 including the ultrasonic jelly (the acoustic coupling media) inside. As the ultrasonic jelly (the acoustic coupling media) supplied to the space between the shielding films 25 and 26 is consumed, gradually flowing, it is also required to direct the patient to supplement ultrasonic jelly by suitably pressing the holder 36 including the ultrasonic jelly inside.

Needless to say, it is natural that the doctor suitably monitors a situation of the remedy of the patient as in other general disease, supplies a new ultrasonic wave radiating apparatus 100 if necessary and continues the remedy.

Second Embodiment

In case medicine having the properties described in above (1) to (3), for example, medicine mainly made of an alkylated derivative of Rose Bengal which is xanthene dye and an ultrasonic wave radiating apparatus low in the degree of convergence are combined, it is important to pay attention that biological reaction is easily caused on an interface on which refraction and scattering are easily caused because there is no difference in ultrasonic intensity between a diseased part and the other part. That is, as the skin of a patient acts as the interface on which refraction and scattering are easily caused in case an ultrasonic wave is radiated from the ultrasonic wave radiating apparatus via the skin, it is important to inhibit the biological action of an ultrasonic wave on the skin.

In the first embodiment, the piezoelectric transducer 32 formed by the plane piezoelectric element to which alternating voltage having a predetermined frequency is supplied is described as a thing for irradiating a patient, however, as disclosed in the U.S. Pat. No. 5,523,058, a waveform advantageous for causing acoustic cavitation can be acquired by superimposing a double frequency on one frequency component. In the invention, the thought can be also utilized, however, from the viewpoint of inhibiting the biological reaction of an ultrasonic wave on the skin, in a second embodiment, ultrasonic waves having different single frequencies shall be radiated toward a target from different sound sources from two directions.

Figure 7A:
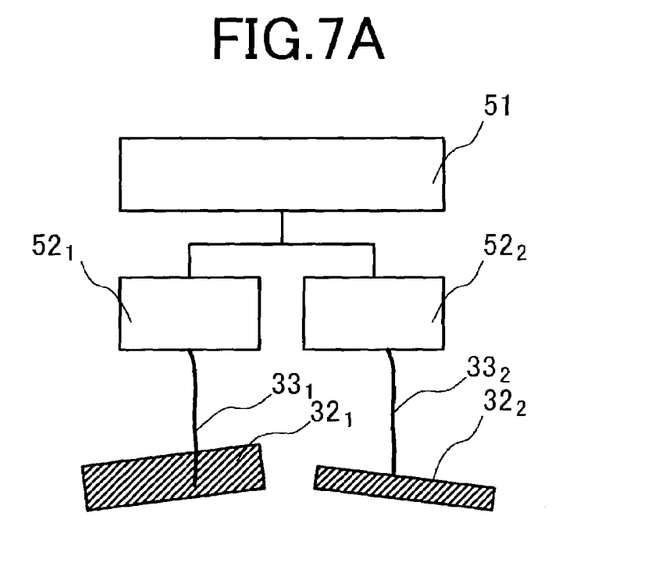
FIG. 7A shows the configuration of a system equivalent to a second embodiment and FIG. 7B is an explanatory drawing for explaining a situation of the propagation of a radiated ultrasonic wave and the result in the second embodiment.
Figure 7B:
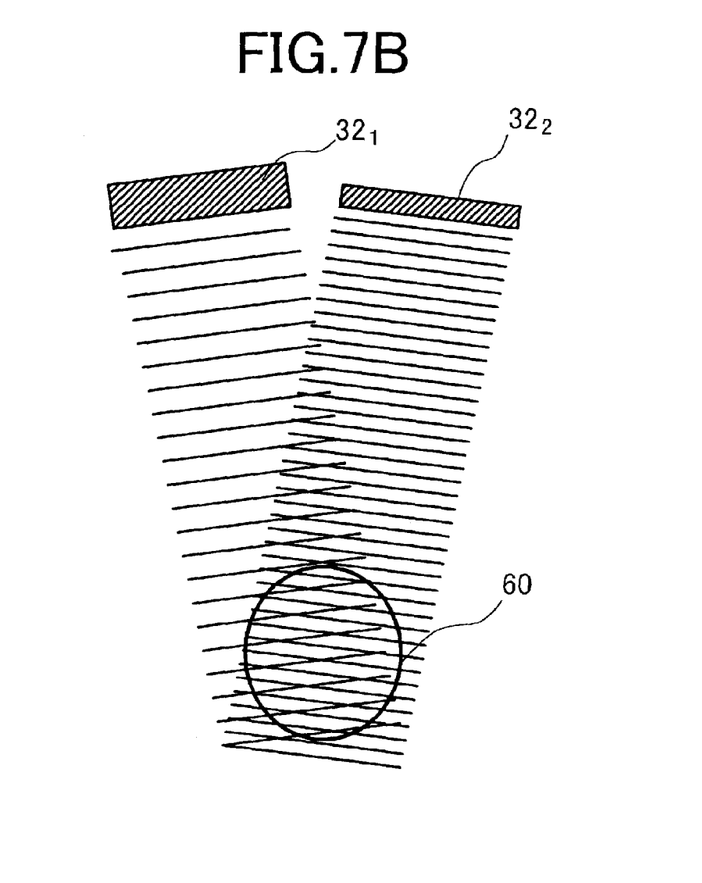

FIG. 7A shows the configuration of a system according to the second embodiment and FIG. 7B is an explanatory drawing for explaining a situation and the result of the propagation of a radiated ultrasonic wave in the second embodiment. Reference numbers 51, 52, 32 and 33 in FIG. 7A are equivalent to the controller mainly formed by the personal computer, the ultrasonic signal generating/amplifying circuit, the piezoelectric transducer and the cable respectively in the first embodiment, however, in the second embodiment, they are different in that the reference numbers having a subscript 1 correspond to a certain frequency and the reference numbers having a subscript 2 correspond to its double frequency. FIG. 7B shows a situation of the propagation of the wave fronts of acoustic waves radiated from two piezoelectric transducers $32_1$ and $32_2$ and a situation in which a part 60 to be remedied is located in a position in which the wave fronts of the respective acoustic waves are overlapped.

As known from FIG. 7B, as frequencies of the respective piezoelectric transducers are merely radiated in positions in which the piezoelectric transducers $32_1$ and $32_2$ are respectively in contact with the skin, an ultrasonic wave in which a double frequency component is superimposed on one frequency component does not act on the skin. However, as the wave fronts of the frequency components radiated by the respective piezoelectric transducers $32_1$ and $32_2$ are overlapped and act at predetermined depth because of the inclination of the piezoelectric transducers $32_1$ and $32_2$, the ultrasonic wave in which the double frequency component is superimposed on one frequency-component acts on the part to be remedied 60, cavitation is effectively caused and medicine mainly made of an alkylated derivative of Rose Bengal which is xanthene dye can be effectively utilized. From the viewpoint of intensity, difference in intensity is made and acoustic intensity on the skin can be reduced such as the skin is irradiated at the intensity of approximately 5 W/cm$^2$ by independently irradiating from two directions, however, a tumor part (the part to be remedied 60) is irradiated at the intensity of approximately 10 W/cm$^2$.

Anti-Tumor effect can be acquired, inhibiting the biological reaction of the following ultrasonic waves on the skin by radiating ultrasonic waves having a specific frequency and its double frequency from plural sound sources and configuring so that each wave is substantially not overlapped on the skin and is overlapped in a tumor region as described above.

In the description referring to FIGS. 7 in the second embodiment, the ultrasonic wave radiating apparatus 100 shown in FIG. 2 and the unit ultrasonic radiator 10 shown in FIGS. 5 respectively in the first embodiment are not described. However, it is evident that in the second embodiment, an ultrasonic wave radiating apparatus 100 in which unit ultrasonic radiators 10 can be suitably installed can be also produced as in the first embodiment. In this case, as described in relation to FIG. 1, when attention is paid to it that in an irradiating apparatus low in the degree of convergence, an ultrasonic wave from a sound source is propagated, spreading, the wave front shown in FIG. 7B is actually spread as a wave advances deep. As a result, an ultrasonic wave in which its double frequency component is superimposed on one frequency component acts on area where the respective irradiation faces of the piezoelectric transducers $32_1$ and $32_2$ are substantially summed in the vicinity of the part to be remedied 60. Therefore, even if the piezoelectric transducer 32 in the unit ultrasonic radiator 10 is divided into the piezoelectric transducers $32_1$ and $32_2$, the similar range to the range covered by the single piezoelectric transducer 32 in the first embodiment can be irradiated.

Needless to say, the system shown in FIGS. 7 may be also composed of two adjacent ultrasonic transducer elements.

Further, it can be arbitrarily selected as in the first embodiment whether the controller 51 mainly formed by a personal computer and ultrasonic signal generating/amplifying circuits $52_1$ and $52_2$ are installed in the cover 31 of the unit ultrasonic radiator 10 or are connected via wiring.

Third Embodiment

Figure 8:
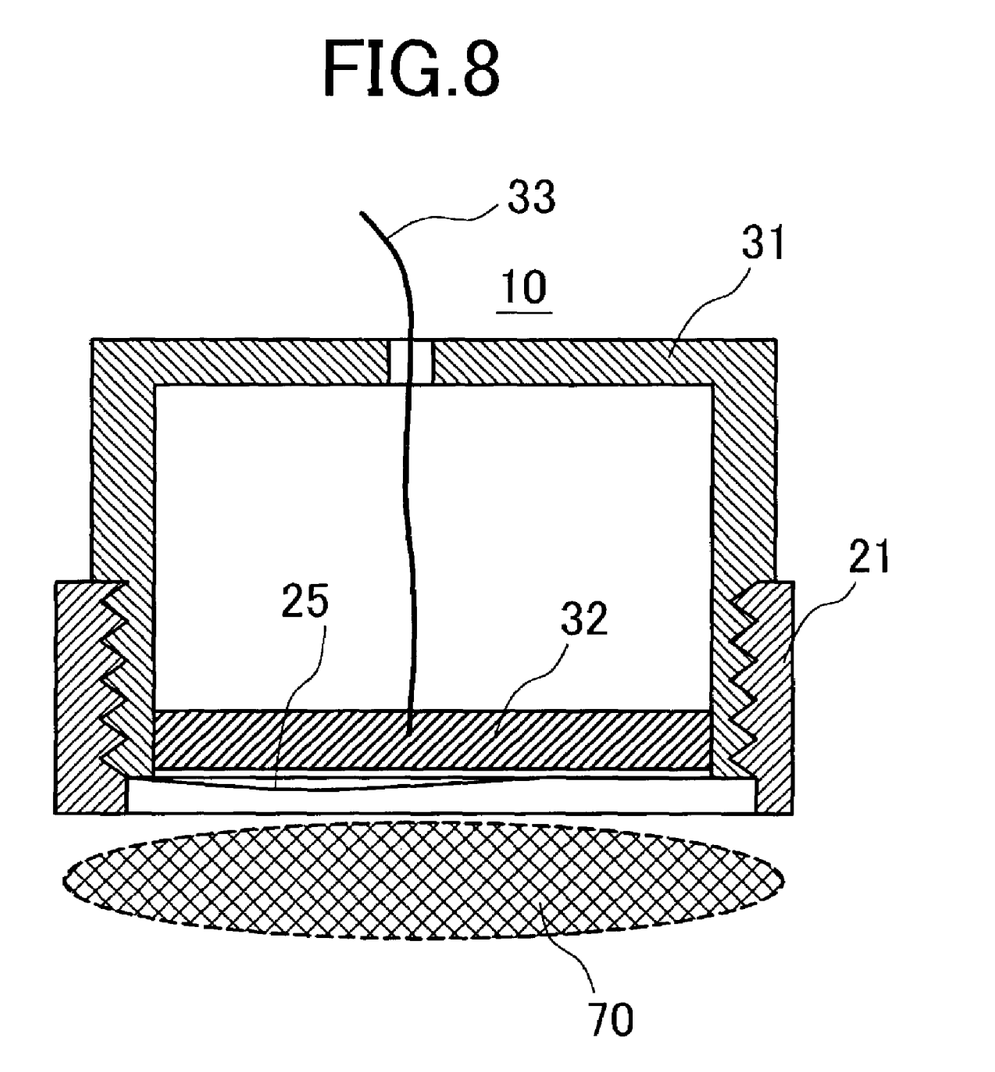
FIG. 8 shows an embodiment in which the ultrasonic transducer element 10 is singly used.

In the first and second embodiments, the ultrasonic wave radiating apparatus 100 is configured by the belt in an arbitrary position of which the ultrasonic transducer element 10 can be mounted, however, the ultrasonic transducer element 10 described in relation to FIGS. 5 can be also independently used. FIG. 8 shows an example of the configuration in this case. FIG. 8 shows an embodiment in which the ultrasonic transducer element 10 shown in FIGS. 5 is used as it is. In case a ultrasonic transducer element is independently used as described above, it is more useful to directly insert a holder 70 including ultrasonic jelly (acoustic coupling media) inside between the skin of a patient and a shielding film 25 of the ultrasonic transducer element 10 than to use the exterior type holder 36 including the ultrasonic jelly (the acoustic coupling media) inside. In this embodiment, therefore, the opening 23, the protrusion 24 and the communicating part 28 (not shown) are not required. The holder 70 is formed by the shielding film 26 made of the cellulose filter of 50 μm and houses ultrasonic jelly inside it.

As air between a piezoelectric transducer 32 and the skin of a patient is removed in case the holder is required to be suitably fixed to a position corresponding to a part to be remedied 60 of the patient, is fixed by a pressure sensitive adhesive tape or both the pressure sensitive adhesive tape and a bandage and is pressed, an ultrasonic wave generated by the piezoelectric transducer can be efficiently transmitted to a diseased part.

Other Embodiment

The representative three embodiments of the invention are described above, however, these can be realized by various embodiments as follows.

The piezoelectric transducer 32 directly transmits an ultrasonic wave to the skin of a patient via the ultrasonic jelly (the acoustic coupling media), however, it is similar to the current various ultrasonic apparatuses that it is useful to provide a suitable matching layer onto the surface on the side of the skin of the piezoelectric transducer 32.

In the first embodiment, the ultrasonic jelly (the acoustic coupling media) is supplied from the exterior type holder 36, however, as in the third embodiment, the expendable holder 70 may be also used.

The extremely thin elastic shielding film 25 is provided to the end near to the substrate 11 of the holder 21, however, this may be also omitted. In this case, the piezoelectric transducer 32 is required to be tightly fitted to the inner surface of the cover 31 so that the ultrasonic jelly (the acoustic coupling media) supplied from the holder 36 is prevented from leaking on the side of the cover 31 through between the piezoelectric transducer 32 and the cover 31.

An ultrasonic wave radiated from a sound source has only to have a frequency and intensity that can be used for causing acoustic cavitation, for the frequency, a basic frequency has only to be in a range of 20 kHz to 1 MHz and its double frequency has only to be in a range of 40 kHz to 2 MHz and for the intensity of the ultrasonic wave, arbitrary values equal to or below 100 W/cm$^2$ can be adopted.

Further, in the above embodiments, a power source is not described, however, it need scarcely be said that a power source is respectively necessary to the controller 51 and the ultrasonic signal generating/amplifying circuit 52 and it is naturally provided. In the embodiment in which the controller 51 and the ultrasonic signal generating/amplifying circuit 52 are installed inside the cover 31, it is desirable that the power source can be also installed inside the cover 31 as a small-sized battery, however, in the case of the shortage of power, a battery is provided inside the cover 35 of the dummy 40 as an exterior type, and the battery and the controller/the ultrasonic signal generating/amplifying circuit are connected via wiring. In case the controller 51, the ultrasonic signal generating/amplifying circuit 52 and the power source can be all installed inside the cover 31, only a switch for activating the personal computer as the controller 51 appears outside the cover 31 and a patient has only to turn on the switch at the timing of the start of remedy.

The above embodiments are described on the premise that a patient is remedied at home, however, it is natural that the invention can be also applied to remedy in a hospital.

As described above, as the ultrasonic apparatus for therapeutical use according to the invention enables remedy by self-management by a patient himself/herself under the direction of a doctor based upon a medical image without depending upon the medical image, it is useful to the remedy at home of the patient.

What is claimed is:

1. An ultrasonic apparatus for therapeutical use, comprising:
    a belt on which transducer-mounting openings of predetermined size are arranged at a predetermined cycle;
    a holder independently fixed to ones of the transducer-mounting openings on one surface of the belt and having substantially the similar opening to each opening of the belt; and
    a cable to supply an electric signal required for an ultrasonic piezoelectric transducer, wherein:
    one holder is provided with a cover held by the holder, and a unit ultrasonic radiator holding the ultrasonic piezoelectric transducer substantially parallel to the face of the opening is formed in the cover, and the ultrasonic piezoelectric transducer is separated into a first and second ultrasonic piezoelectric transducers wherein wave fronts of ultrasonic waves generated by the first and second ultrasonic piezoelectric transducers are inclined in directions in which the wave fronts are overlapped and the first ultrasonic piezoelectric transducer is excited by a first frequency and the second ultrasonic piezoelectric transducer is excited by a second frequency which is substantially double a frequency of the first frequency.

2. An ultrasonic apparatus for therapeutical use according to claim 1, wherein:
    a thin film having minute holes and completely covering the opening is stuck to respective openings on a body-facing surface of the belt.

3. An ultrasonic apparatus for therapeutical use according to claim 2, wherein: the holder is provided with lubricant-access opening;
    the holder is provided with a protrusion provided in the lubricant-access opening and communicating with space between the piezoelectric transducer and the thin film; and
    an acoustic-coupling-media reservoir communicating with the protrusion to supply acoustic coupling media to the space via the protrusion.

4. An ultrasonic apparatus for therapeutical use according to claim 1, wherein:
    a cover for covering the opening of the holder is provided to a holder that has no ultrasonic transducer element.

5. An ultrasonic apparatus for therapeutical use according to claim 1, wherein:
    a controller for controlling the ultrasonic piezoelectric transducer and an amplifier for a signal for exciting the ultrasonic piezoelectric transducer are built in the cover; and
    a starting switch is provided to the outside face of the cover.

6. An ultrasonic apparatus for therapeutical use, comprising:
    a belt on which transducer-mounting openings of predetermined size are arranged at a predetermined cycle;
    a holder independently fixed to ones of the transducer-mounting openings; and
    a cable to supply an electric signal required for an ultrasonic piezoelectric transducer, wherein:
    one holder is provided with a cover held by the holder, and a unit ultrasonic radiator holding the ultrasonic piezoelectric transducer, and the ultrasonic piezoelectric transducer is separated into a first and second ultrasonic piezoelectric transducers wherein wave fronts of ultrasonic waves generated by the first and second ultrasonic piezoelectric transducers are inclined in directions in which the wave fronts are overlapped and the first ultrasonic piezoelectric transducer is excited by a first frequency and the second ultrasonic piezoelectric transducer is excited by a second frequency which is substantially double a frequency of the first frequency to induce cavitation.

7. An ultrasonic apparatus for therapeutical use according to claim 6, wherein:
    a thin film having minute holes and covering the opening is stuck to respective openings on a body-facing surface of the belt.

8. An ultrasonic apparatus for therapeutical use according to claim 7, wherein:
    the holder is provided with lubricant-access opening; the holder is provided with a protrusion provided in the lubricant-access opening and communicating with space between the piezoelectric transducer and the thin film; and
    an acoustic-coupling-media reservoir communicating with the protrusion to supply acoustic coupling media to the space via the protrusion.

9. An ultrasonic apparatus for therapeutical use according to claim 6, wherein:
    a cover for covering the opening of the holder is provided to a holder that has no ultrasonic transducer element.

10. An ultrasonic apparatus for therapeutical use according to claim 6, wherein:
    a controller for controlling the ultrasonic piezoelectric transducer and an amplifier for a signal for exciting the ultrasonic piezoelectric transducer are built in the cover; and
    a starting switch is provided to the outside face of the cover.

11. An ultrasonic apparatus for therapeutical use, comprising:
    a belt on which transducer-mounting openings of predetermined size are arranged at a predetermined cycle;
    a holder independently fixed to ones of the transducer-mounting openings; and
    a cable to supply an electric signal required for an ultrasonic piezoelectric transducer, wherein:
    a first holder is provided with a cover held by the holder, and a first unit ultrasonic radiator holding a first ultrasonic piezoelectric transducer, a second holder is provided with a cover held by the holder, and a second unit ultrasonic radiator holding a second ultrasonic piezoelectric transducer, wherein wave fronts of ultrasonic waves generated by the first and second ultrasonic piezoelectric transducers are inclined in directions in which the wave fronts are overlapped and the first ultrasonic piezoelectric transducer is excited by a first frequency and the second ultrasonic piezoelectric transducer is excited by a second frequency which is substantially double a frequency of the first frequency to induce cavitation.

12. An ultrasonic apparatus for therapeutical use according to claim 11, wherein:

a thin film having minute holes and covering the opening is stuck to respective openings on a body-facing surface of the belt.

13. An ultrasonic apparatus for therapeutical use according to claim 12, wherein:

the holder is provided with lubricant-access opening; the holder is provided with a protrusion provided in the lubricant-access opening and communicating with space between the piezoelectric transducer and the thin film; and an acoustic-coupling-media reservoir communicating with the protrusion to supply acoustic coupling media to the space via the protrusion.

14. An ultrasonic apparatus for therapeutical use according to claim 11, wherein:

a cover for covering the opening of the holder is provided to a holder that has no ultrasonic transducer element.

15. An ultrasonic apparatus for therapeutical use according to claim 11, wherein:

a controller for controlling the ultrasonic piezoelectric transducer and an amplifier for a signal for exciting the ultrasonic piezoelectric transducer are built in the cover; and a starting switch is provided to the outside face of the cover.

* * * * *